United States Patent [19]

Newman

[11] Patent Number: 5,035,514

[45] Date of Patent: Jul. 30, 1991

[54] THERMAL PROBE FOR MEASURING THERMAL PROPERTIES OF A FLOWING MEDIUM

[75] Inventor: William H. Newman, Jamaica Plain, Mass.

[73] Assignee: Thermal Technologies, Inc., Cambridge, Mass.

[21] Appl. No.: 520,100

[22] Filed: May 7, 1990

[51] Int. Cl.⁵ .................... G01F 1/68; G01K 13/02
[52] U.S. Cl. ............................ 374/164; 73/204.19; 338/23
[58] Field of Search ............... 374/164, 169, 135; 73/204.18, 295, 204.19; 338/23; 73/295, 204.19;

[56] References Cited

U.S. PATENT DOCUMENTS

| | | | |
|---|---|---|---|
| 3,321,974 | 5/1967 | Sterbutzel | 374/164 X |
| 3,491,596 | 1/1970 | Dean | 374/164 X |
| 3,552,210 | 1/1971 | Wright, Jr. | 374/184 X |
| 3,559,883 | 2/1971 | Buiting | 374/185 X |
| 3,832,902 | 9/1974 | Usami et al. | 374/164 |
| 4,059,982 | 11/1977 | Bowman | 73/204.18 |
| 4,408,902 | 10/1983 | Peuker | 374/164 X |

Primary Examiner—Daniel M. Yasich
Attorney, Agent, or Firm—Robert F. O'Connell

[57] ABSTRACT

A device for heating a medium with which the device is in thermal contact for use in determining the thermal or flow properties of the medium. The device has a heater for supplying heat to the medium at an interface of the device with the medium and a temperature sensor for sensing the temperature at such interface.

9 Claims, 4 Drawing Sheets

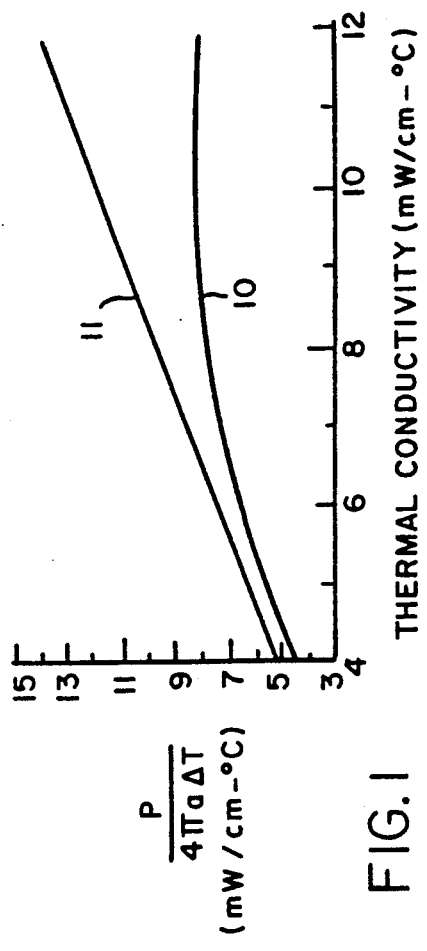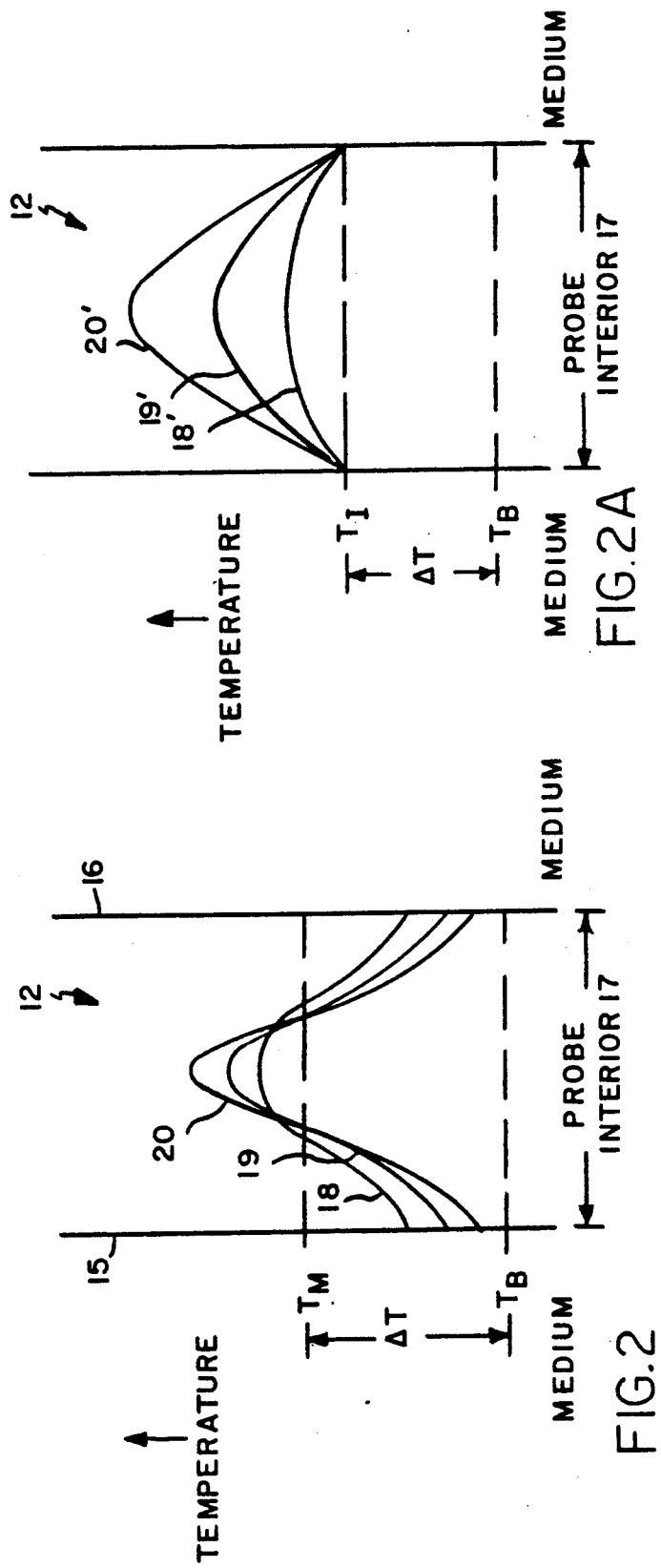

THERMAL PROBE FOR MEASURING THERMAL PROPERTIES OF A FLOWING MEDIUM

Introduction

This invention relates generally to thermal probes and, more particularly, to thermal probes for use in providing measurements of the thermal properties of a flowing medium.

BACKGROUND OF THE INVENTION

It is often desirable to determine the thermal properties of a medium through which fluid may flow, such as is the case for blood flowing in body tissue, for example. Such properties include the thermal conductivity and the perfusion, i.e., blood flow, thereof. Two exemplary systems for such purpose have been described in U.S. Pat. No. 4,059,982, issued to H. F. Bowman on Nov. 29, 1977 and U.S. Pat. No. 4,852,027, of H. F. Bowman et al., issued on July 25, 1989.

In such systems a thermal transducer probe is inserted into, or positioned adjacent to, a medium whose properties are to be determined. The probe is normally in the form of an approximately spherical thermistor bead which is used both as a heating element and as a temperature sensing element. By passing a small current through the thermistor, temperature is passively sensed by the thermistor to establish a baseline temperature. During a subsequent heating mode a relatively larger current is passed through the thermistor to produce a resistive, or ohmic, heating thereof which is sufficient to maintain the mean volumetric temperature of the transducer at a specified incremental level above the baseline temperature. Such heating operation transfers heat energy to the medium whose thermal characteristics are to be determined. Measurements of the electrical power required to heat the thermal transducer probe and, thereby, the medium to the higher temperature level can then be made and used in a suitably programmed data processor to compute the thermal conductivity and the perfusion characteristics of the medium, as described in the aforesaid Bowman et al. patents.

The thermal transducer probe used in such systems presents a characteristic non-linear response of the heating power to the thermal conductivity $k_m$ of the medium, for example, and normally exhibits relatively low response sensitivity. Typically the non-linear power vs. conductivity response curves of exemplary devices are such that the inverse of the probe heating power is proportional to the inverse of the thermal conductivity of the medium. The general slope of the overall curve over its useful range tends to be relatively low, thereby indicating a generally low response sensitivity. Moreover, the probe displays a "saturation" effect which is such as to produce a further decrease in measurement sensitivity as the medium thermal conductivity increases, i.e., in effect the slope of the curve becomes relatively lower with an increase in thermal conductivity. Similarly, a non-linear and a low sensitivity response of heating power to perfusion also occurs.

The basis for the low sensitivity of such a probe can be understood in terms of effect of the temperature at the interfacial surface of the probe with the medium. As the medium thermal conductivity increases, the temperature at the thermistor/medium interface decreases since the medium environment surrounding the thermistor probe becomes more efficient in extracting thermal energy from the thermistor probe. Accordingly, as the thermal conductivity of the media increases, the measurable temperature field produced by the probe tends not to extend very far into the medium and transducer heating power becomes to a greater extent determined by transducer, rather than medium, thermal properties. Hence, the transducer's ability to thermally "interrogate" the medium becomes less effective, resulting in a thermal saturation effect.

Such undesired non-linearity and lower sensitivity response effects in previously used thermistor probes is a direct consequence of the transducer design, such probes being designed to regulate the transducer mean volumetric temperature rather than the temperature field within the medium whose thermal properties are under investigation. It is desirable to design a thermal transducer probe which provides effectively linear responses to heater power and which does not produce a reduced measurement response sensitivity as the thermal conductivity or perfusion of the medium increases. With such a probe it should be possible to simplify the computations necessary to determine the thermal properties of the medium under investigation and to provide a relatively high response sensitivity.

BRIEF SUMMARY OF THE INVENTION

In accordance with the invention a thermal transducer probe is designed so that heat energy is extracted from the probe into the medium; while simultaneously the interfacial temperature of the probe with the medium is measured. The rate of heat extraction is controlled so that the maximum temperature of the medium, which occurs at the probe/medium interface, is maintained at a desired level with respect to a reference, or baseline, temperature. Such design can be contrasted with prior probe designs in which heat energy is extracted from the probe into the medium at a rate which is controlled so that the probe temperature, averaged over the volume thereof, is held at a constant temperature level.

In order to achieve such operation, a thermal transducer probe in accordance with a preferred embodiment of the invention is designed so that separate heating and sensing elements are used therein, in contrast with the use of a single element for both heating and sensing operations in previously used probes.

In one preferred method of operation, by maintaining the interface temperature at a desired value with respect to a baseline temperature, independently of the thermal characteristics of the medium, the thermal power response as a function of thermal conductivity or perfusion is essentially linear in nature and the response sensitivity thereto remains relatively high over the ranges of thermal conductivity and perfusion of interest, without the presence of saturation effects in the response.

DESCRIPTION OF THE INVENTION

The invention can be described in more detail with the help of the accompanying drawings wherein FIG. 1 shows a graph of the power vs. thermal conductivity response curves for typical probes of the prior art and of the invention, respectively;

FIGS. 2 and 2A show temperature profiles within a cross-section of probes of the prior art and of the invention, respectively;

Figure 3:
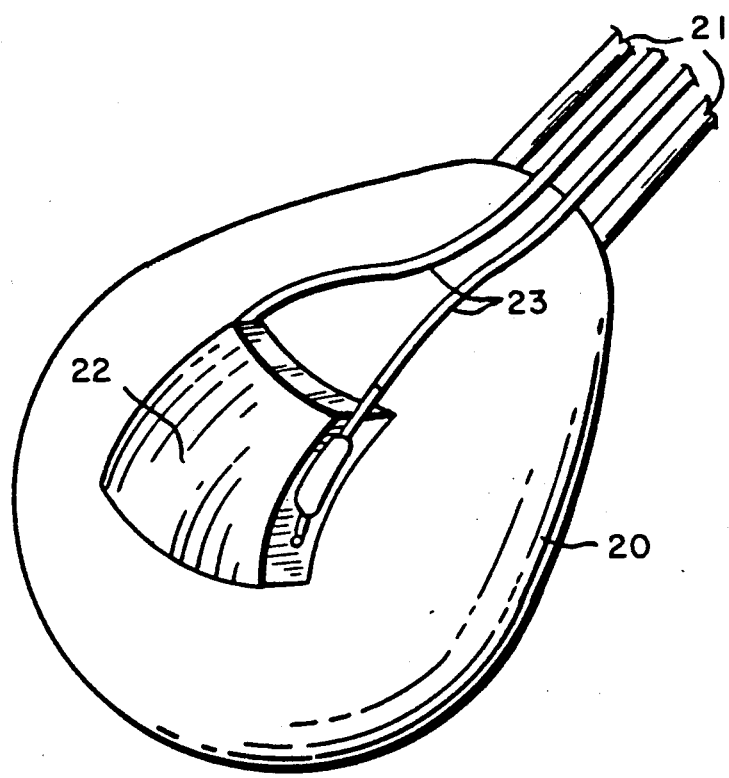
FIGS. 3 and 3A show pictorial and sectional views, respectively, of two exemplary embodiments of probes of the invention.

As a help in understanding the advantages of a probe of the invention, particularly as constrasted with previously used probes, FIG. 1 illustrates a typical exemplary heating power vs. thermal conductivity response curve 10 of a previous probe such as described in the aforesaid patents. As illustrated, the power level is normalized and expressed as $P/4\pi a \Delta T$, where a is the radius of the probe and $\Delta T$ is the change in the mean volumetric temperature of the probe with respect to an initial baseline temperature. As can be seen therein, the response curve 10 is non-linear in nature, such response being found to be such that the inverse of probe heating power is essentially proportional to the inverse of the thermal conductivity of the medium, as mentioned above. Moreover, the overall sensitivity is relatively low, tending to decrease as the thermal conductivity increases.

The reason for the low sensitivity of such a probe is best illustrated in FIG. 2 which depicts various temperature profiles across a probe cross-section 12 for different thermal conductivities of the medium in which it is immersed. As can be seen therein, the interfaces at the surface of the probe and the medium are shown diagrammatically at each side of cross-section region 12, i.e., at surface interfaces 15 and 16, the interior 17 of the probe being shown therebetween. Exemplary temperature profile curves 18, 19 and 20 illustrate at a qualitative manner typical interior temperature profiles from one side to the other of the probe when the mean, volume-averaged temperature in the thermistor bead rises to, and is held at, a value $T_M$, which is $\Delta T$ above an established baseline temperature value $T_B$. Curve 18, for example, represents a temperature profile within the bead when used with a medium having a relatively low thermal conductivity, curve 19 for a medium having a higher thermal conductivity, and curve 20 for a medium having a still higher thermal conductivity.

Thus, as the thermal conductivity of the medium increases, the temperature at the thermistor/medium interface, i.e., at surfaces 15 and 16, decreases since the medium environment surrounding the thermistor probe becomes more efficient in extracting thermal energy therefrom. Accordingly, as the thermal conductivity of the medium increases, the measurable temperature field produced by the probe tends not to extend very far into the medium and the transducer's ability to thermally "interrogate" the medium becomes less effective, resulting in a thermal saturation effect, as discussed above.

FIG. 2A shows exemplary temperature profiles 18', 29', 20' which are achieved in accordance with the probe of the invention. As can be seen therein, the temperature profiles within such a probe for increasing thermal conductivity of the medium are such that the temperature $T_I$ at the interface between the probe and the medium is always maintained at a fixed temperature level $\Delta T$ above a baseline temperature $T_B$. By maintaining the interface temperature at such a fixed value, in effect independent of the thermal conductivity of the medium, the thermal power response as a function of thermal conductivity becomes essentially linear and the sensitivity remains relatively high and relatively constant, as discussed in more detail below.

Figure 9:
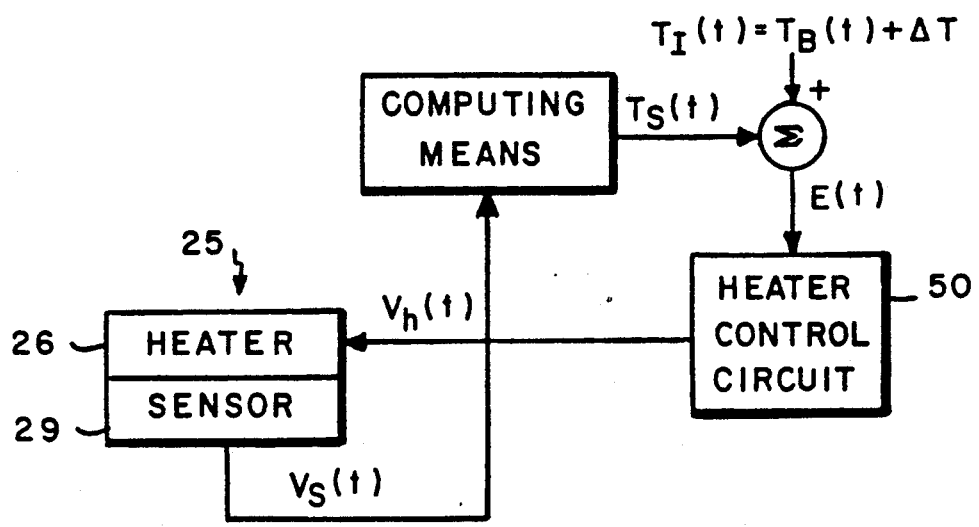
FIG. 9 shows a block diagram of a control circuit for use in controlling the interface temperature in accordance with the invention.

FIG. 9 depicts a simple block diagram of a control system, the implementation of what would be well known to those in the art, for maintaining the interface temperature as sensed by a sensor element 29 of a probe 25 at the desired level $\Delta T$ above a baseline temperature $T_B(t)$. Thus, the sensor voltage output $V_S(t)$ representing the sensed interface temperature is supplied to a computing means which in turn provides a computed output signal $T_S(t)$ representative of the sensed temperature which signal is compared to a signal $T_I(t)$ which is representative of the desired interface temperature, i.e., a signal which represents a baseline temperature $T_B(t)$ and a temperature difference $\Delta T$ above the base temperature. An error signal $E(t)$ is supplied to a heater control circuit 50 for supplying a heater voltage $V_h(t)$ to heat element 26 of probe 25 to maintain the interface temperature at the desired level.

FIG. 3 shows an exemplary embodiment of a thermal transducer probe in accordance with the invention. As can be seen therein, a thermistor bead 20 of the type generally used and described with respect to the systems set forth in the aforesaid Bowman patent, for example, is used for heating a medium in which it is immersed, the thermistor bead being supplied with appropriate electrical power for such purpose from a source thereof (not shown) via electrical leads 21, as would be well known to the art.

In addition, a relatively thin thermistor sensing element 22, which can sometimes be referred to as a "sensing flake" thermistor, is mounted on and suitably adhered to the surface of the thermistor heater bead 20. The sensing thermistor element 22 provides a signal at leads 23 proportional to the temperature at the surface of thermistor bead 20, i.e., in effect at the surface/medium interface when immersed in a medium.

Figure 3A:
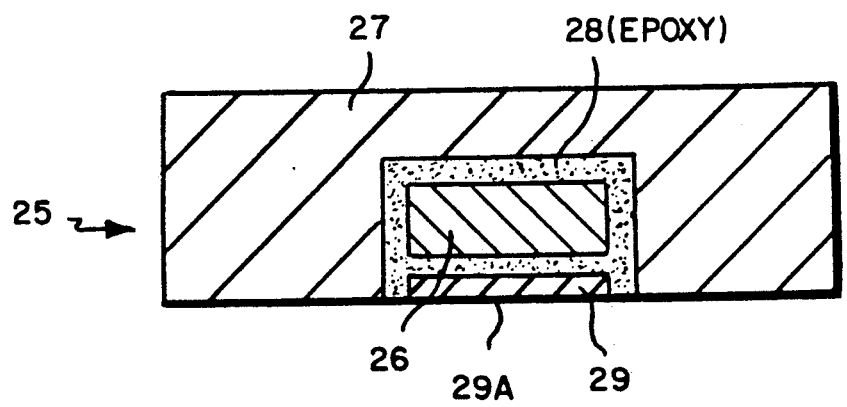

Alternatively, a planar thermistor structure is shown diagrammatically in cross section in FIG. 3A, a planar thermistor heater element 26 being positioned within an insulative region 27 of an overall structure 25, heater 26 being itself embedded in a thermally conductive epoxy layer 28. A thermistor sensing element 29 is partially embedded in epoxy layer 28 with its sensing surface 29A in contact with the medium in which the overall probe is immersed. Heater leads and sensed voltage leads, not specifically shown, can be appropriately connected to heater element 26 and sensing element 29 as desired.

Curve 11 of FIG. 1 shows a typical exemplary response curve which depicts the heater power required to maintain the surface temperature at a level $T_I$ (i.e., $\Delta T$ above a baseline temperature $T_B$), as a function of the thermal conductivity of the medium. As can be seen by curve 11, the response is essentially linear in nature and maintains a relatively high sensitivity response over a wide range of medium thermal conductivity, which response does not saturate at high thermal conductivities. The exemplary response curves as depicted in FIG. 1 for both a prior probe (curve 10) and a probe of the invention (curve 11) were obtained 10 seconds after heating power has been applied.

Figure 4:
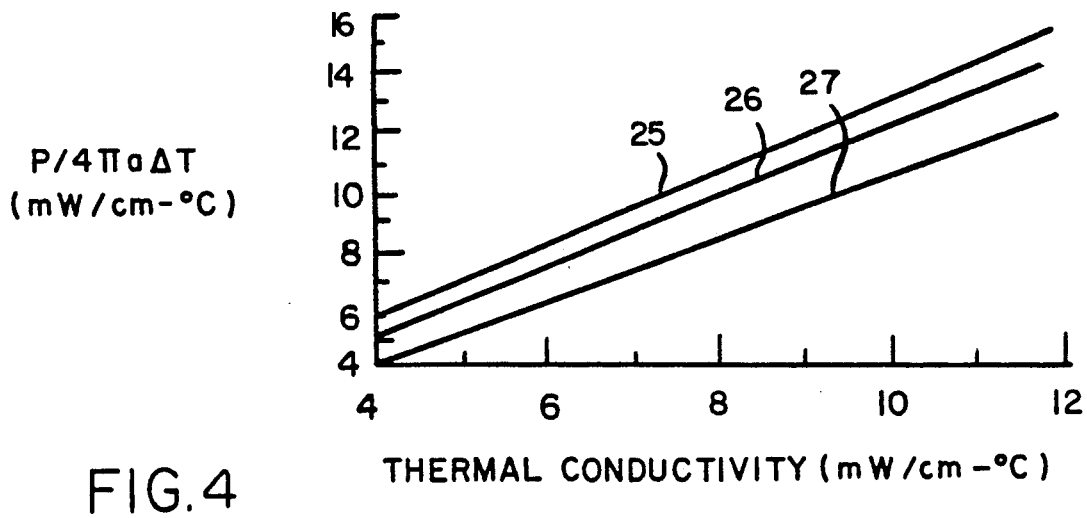
FIG. 4 shows a graph of power vs. thermal conductivity response curves for a probe of the invention taken at different times following the application of power thereto.

FIG. 4 shows, in an alternative manner, power vs. thermal conductivity response curves for a probe of the invention at different heating times after heating power is applied e.g., after 4 seconds (curve 25), after 10 seconds (curve 26), and at a steady state condition (after approximately 120 seconds, or greater) (curve 27). In each case the response curve is essentially linear and maintains an effectively constant and relatively high slope or sensitivity. It has been found that while essentially strict linearity is observed at steady state conditions, deviations from linearity are still relatively minimal at the lesser or transient measurement times, e.g., maximum deviations from linearity at 10 seconds being only 0.3% and at 4 seconds being only marginally greater at 0.4%. Since the linear response and high sensitivity characteristics are not compromised by taking measurements at times, or during transient intervals, relatively shortly after heat energy is applied, the effect of drifts or fluctuations in baseline temperature can be minimized by using reduced experimental durations.

Figure 5:
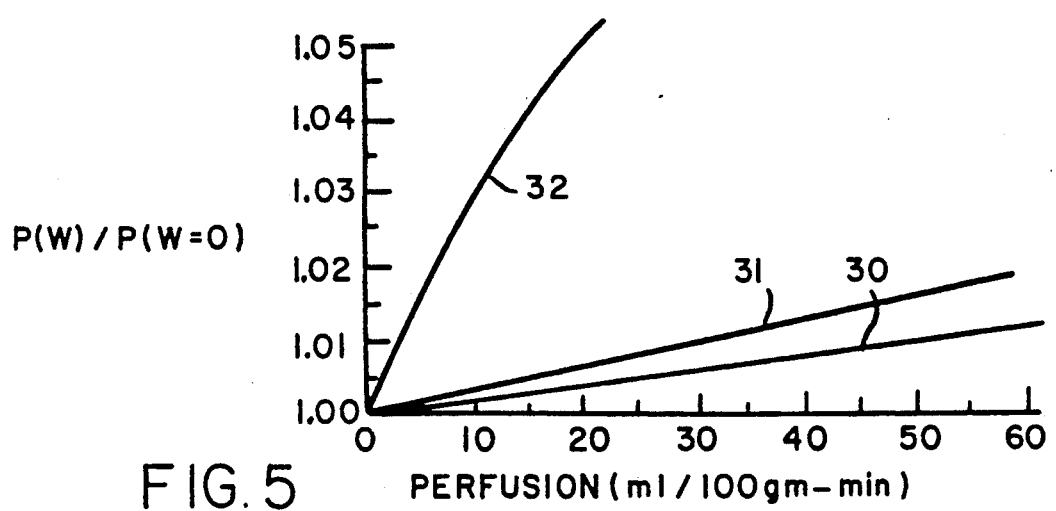
FIG. 5 shows a graph of power vs. perfusion response curves for a probe of the invention taken at different times following the application of power thereto.

The effect on perfusion measurements, when using a thermal transducer probe in accordance with the invention, can be described by comparing the curves set forth in FIG. 5. In such graph, power is normalized to power at non-flow conditions (perfusion, W-O). For a probe of the invention, the power vs. perfusion responses are shown in FIG. 5 at 4 seconds (curve 30) 10 seconds (curve 31), and at steady state (curve 32). While the steady state response thereof is clearly more sensitive to perfusion (having a much higher slope) than at the lesser or transient time measurements, the non-linear, parabolic nature thereof is evident in curve 32. When using a probe of the invention, a square-root relationship between probe heating power and perfusion exists at steady-state conditions, as it does also when using probes of previous constructions discussed in the aforesaid patents. For transient measurements, however, the linearity is more nearly perfect with maximum deviations therefrom of 0.7% at 10 seconds and 0.3% at 4 seconds. The response sensitivity of the probe to perfusion is also considerably enhanced as compared to designs described in the aforesaid patents which maintain a constant volume averaged temperature increment, such sensitivity being 2.4 times more sensitive at 4 seconds and 2.1 times more sensitive at 10 seconds.

In considering the curves of FIG. 5 for probes of the invention, it is noted that, while shorter heating times improve linearity of the response to perfusion and lessen the effects of baseline drifts or fluctuations in temperature thereon, longer heating time measurements do increase the sensitivity of the response to perfusion. Thus a compromise can be reached in any practical system between the desire for relatively high response sensitivity and the desire for rapid measurements, linearity, and immunity from baseline variations.

Figure 6:
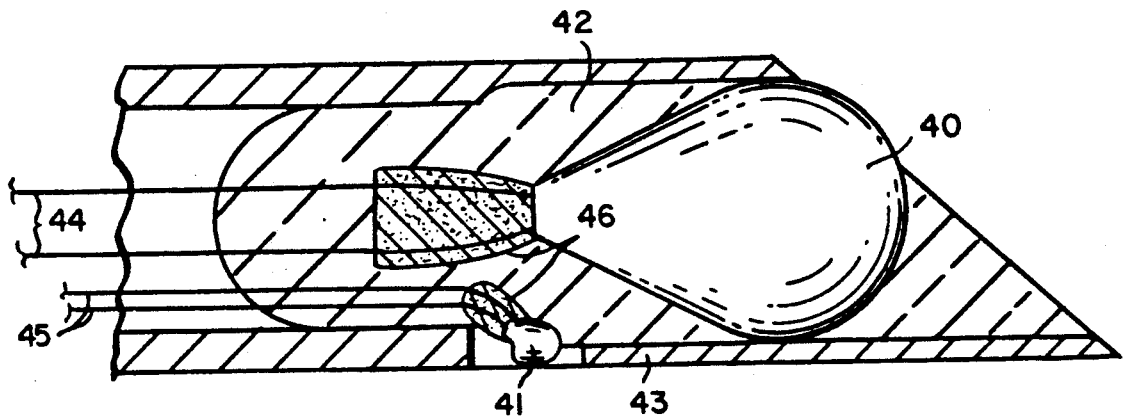
FIG. 6 shows a view in section of an alternative embodiment of a probe of the invention as used in a catheter shaft configuration.

Thermal probes are often positioned within a medium, such as blood tissue, by mounting the probe at the end of a metallic catheter needle shaft, which shaft is relatively highly thermally conductive and is inserted into the soft biological material or medium. One exemplary embodiment thereof is depicted in FIG. 6. As seen therein, a probe of the invention includes a thermistor heater element 40 and a separate thermistor sensing element 41. The heater element 40 is substantially embedded in a conductive epoxy material 42 which is encased in the tip end of a steel catheter shaft 43. At least a part of the heater element 40 may be directly exposed, as shown, to a medium into which the tip of the shaft is immersed to supply heat energy directly thereto, as well as indirectly to the medium via the conductive epoxy material 42. The separate thermistor sensing element 41 is also partially embedded in epoxy material 42 and has a surface thereof directly exposed to the medium, as shown. Appropriate heater leads 44 are connected to heater element 40 for connecting said element to a source of energy therefor and appropriate sensor leads 45 are connected to sensing element 41 to connect the sensed signal therefrom to appropriate circuitry for subsequent use, the relatively fragile ends of such leads each being embedded in an electrically non-conductive epoxy material 46 for mechanical strength and protection.

In order to further demonstrate the advantages of a probe in accordance with the invention in such a thermally conductive shaft structure, it is helpful to consider the effects of thermal conduction along such a catheter needle shaft on the measurements involved, particularly where the shaft has a finite thermal conductivity substantially greater than that of the tissue into which it is inserted.

Figure 7:
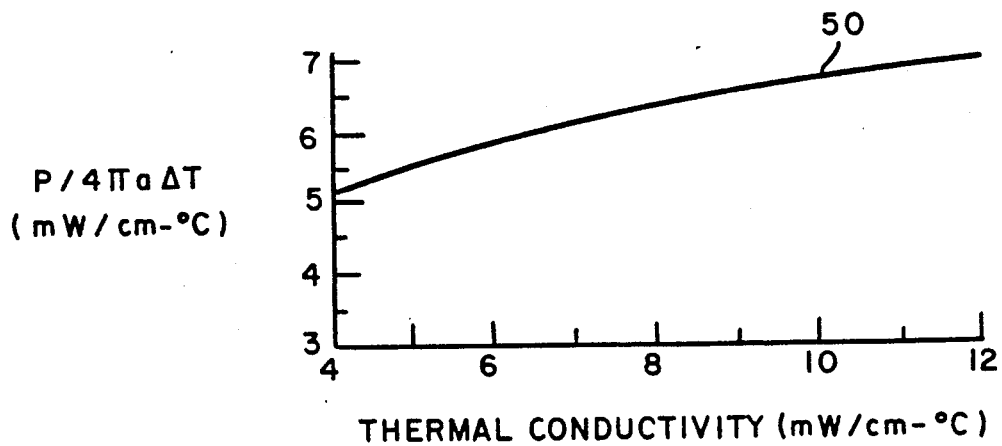
FIGS. 7 and 8 show graphs of power vs. thermal conductivity response curves showing the effects of the presence of thermally conductive catheter shafts thereon for probes of the prior art and of the invention, respectively.
Figure 8:
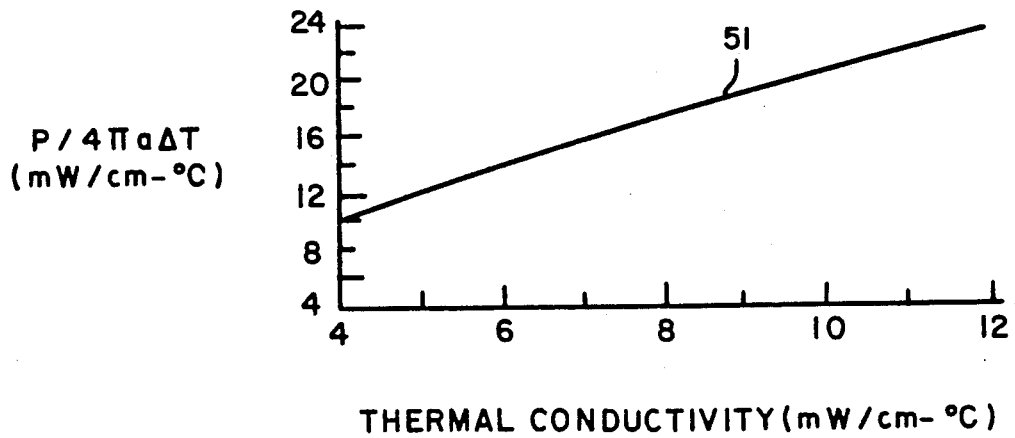

The effects of mounting a probe at the tip of such a shaft are shown in FIGS. 7 and 8, for a prior art probe and for a probe of the invention, respectively, when using a transient measurement heating time of 10 seconds. The response linearity and sensitivity of heating power as a function of thermal conductivity of a prior art transducer, (FIG. 7), is severly degraded as to its sensitivity and linearity by the presence of the steel mounting shaft. In FIG. 8, on the other hand, the power vs. thermal conductivity response of a transducer of the invention has a substantially linear response, as well as a relatively high sensitivity, as shown by curve 51 in FIG. 8 (the differences int he scales used for power in FIGS. 7 and 8 should be noted). In general, response sensitivity for probes of the invention have been found to be at least twice that of prior probes in the absence of a metallic mounting shaft and at least three times that of prior probes when the effects of metallic mounting shafts are included.

The difference in such responses can be better understood in terms of the different techniques for controlling the temperatures involved. When volumetric mean temperatures of a probe are controlled to be at a fixed level above a baseline temperature, a significant amount of heat energy is carried away from the medium by the thermally conductive shaft member, such energy never reaching the medium so that it cannot be used, in effect, to "interrogate" the medium. In contrast, when the probe medium interface temperature is controlled to be at a fixed level above a baseline temperature, although more heating power is required to account for whatever heat is carried away by the shaft, no significant loss of measurement sensitivity occurs when the interface temperature is controlled to be maintained at such fixed level. In effect, the thermal transducer probe of the invention is designed so that the actual tissue temperature field can be regulated and not the average internal probe temperature as in prior probe designs.

In summary, a thermal transducer probe in accordance with the invention achieves a substantially linear response to thermal conductivity and tissue perfusion. Moreover, such a transducer probe provides greater sensitivity to thermal conductivity and tissue perfusion measurements and is relatively independent of transducer thermal properties or mounting shaft thermal effects. Accordingly, such a probe design avoids any loss of sensitivity in measuring the desired medium properties which would otherwise occur because of such effects.

The provision of a linear transducer response also permits the electronic and analysis procedures required to perform accurate thermal property blood flow measurements to be simplified. Further, since such linear response is provided for short measurement times, i.e., effectively during the transient time period after power is applied, rather than at a steady state condition, following the application of power, a system using such a probe can provide relatively rapid, repetitive, quasi-continuous measurements and the results monitored in real-time, thereby allowing for a close monitoring of rapid changes in thermal properties of the medium. For example, a close monitoring of rapid changes in the thermal characteristics of tissue due to the effects of drug delivery on tissue blood flow can be made. Further there is no "saturation" effect, or loss of sensitivity which normally occurs with prior probes as the thermal conductivity or perfusion of the medium increases.

By combining greater sensitivity and linearity offered by the probe of invention with the precision instrumentation, thermal model, and data analysis schemes such as described in the aforesaid Bowman et al. patents, it has been found that the aforesaid measurement technique can be enhanced by changes in probe design alone which permits dramatic increases in measurement accuracy. Further, by assuring the relative insensitivity of a thermal transducer probe of the invention to mounting shaft thermal effects, a relatively sturdy, metallic needle-type probe may be employed with little or no decrease in measurement response sensitivity.

While the embodiments disclosed above represent preferred embodiments of the invention, modifications thereto may occur to those in the art within the spirit and scope of the invention. Hence the invention is not to be construed as limited to the specific embodiments described above except as defined by the appended claims.

What is claimed is:

1. A probe device for heating a medium with which said device is in thermal contact for use in determining the thermal conductivity and diffusivity of said medium when no fluid is flowing therein and for determining the flow properties of said medium, including the effective thermal conductivity, the effective thermal diffusivity, or perfusion thereof when a fluid is flowing therein, said device comprising
    a heater near or on said probe device for supplying heat to said medium at an interface of said device with said medium;
    a temperature sensor associated with said interface for sensing the temperature at said interface;
    control means connected to said probe device for maintaining the temperature at said interface substantially at a selected level with said probe device with respect to a reference temperature independently of the thermal characteristics of said medium.

2. A device in accordance with claim 1 wherein
    said heater is a thermistor bead in thermal contact with said medium at said interface and said temperature sensor is in direct thermal contact with said medium substantially at a selected region of said interface.

3. A device in accordance with claim 2 wherein said temperature sensor is mounted on the surface of said thermistor bead.

4. A device in accordance with claim 1 wherein said heater is embedded in a layer of material which layer is in direct thermal contact with said medium at said interface and said temperature sensor is partially embedded in said layer, so as to be in direct thermal contact with said medium at said interface.

5. A device in accordance with claim 1 and further including an insertion means, said device being mounted at the end of said means for insertion in said medium.

6. A device in accordance with claim 5 wherein
    said heater means is partially embedded in a first region of a material, a portion of said heater means and a portion of said material being in direct thermal contact with said medium; and
    said temperature sensor is partially embedded in said material, a portion of said sensor being in direct thermal contact with said medium.

7. A device in accordance with claim 6 and further including
    heater leads for connecting said heater means to a source of energy; and
    sensor leads connected to said sensor for providing a sensed signal from said sensor,
    said heater leads and said sensor leads being partially embedded in electrically non-conductive material within said material.

8. A method of using a probe for heating a medium for use in determining the thermal conductivity and diffusivity of said medium when no fluid is flowing therein and for determining the flow properties of said medium, including the effective thermal conductivity, the effective thermal diffusivity, or perfusion thereof when a fluid is flowing therein, said method comprising the steps of
    applying heat via a heater element new or on said probe to a medium at an interface of said heater element and said medium;
    sensing the temperature of the medium at or near said interface; and
    controlling the application of heat from the probe to said medium in response to said sensed temperature to maintain the temperature at said interface at a selected value with respect to a reference temperature independently of the thermal characteristics of said medium.

9. A method in accordance with claim 8 wherein the temperature is maintained at a constant value above a baseline temperature.

* * * * *